US010259640B2

(12) United States Patent
Yao et al.

(10) Patent No.: US 10,259,640 B2
(45) Date of Patent: Apr. 16, 2019

(54) TEST-STRIP STORAGE VIAL

(71) Applicant: Sinocare Inc., Changsha, Hunan (CN)

(72) Inventors: Nianlong Yao, Hunan (CN); Feng Hu, Hunan (CN); Xiaohua Cai, Hunan (CN)

(73) Assignee: Sinocare Inc. (CN)

(*) Notice: Subject to any disclaimer, the term of this patent is extended or adjusted under 35 U.S.C. 154(b) by 0 days.

(21) Appl. No.: 15/212,816

(22) Filed: Jul. 18, 2016

(65) Prior Publication Data

US 2017/0166388 A1    Jun. 15, 2017

(30) Foreign Application Priority Data

Dec. 10, 2015  (CN) .................... 2015 2 1020364 U

(51) Int. Cl.
*B65D 83/08* (2006.01)
*G01N 33/487* (2006.01)

(52) U.S. Cl.
CPC ..... *B65D 83/0829* (2013.01); *B65D 83/0817* (2013.01); *G01N 33/48757* (2013.01); *G01N 33/48778* (2013.01)

(58) Field of Classification Search
CPC ............ B65D 83/0823; B65D 83/0829; G01N 33/48757; G01N 33/48778
See application file for complete search history.

(56) References Cited

U.S. PATENT DOCUMENTS

| 3,405,841 | A | * | 10/1968 | Barr, Sr. ................. | A61M 5/32 221/232 |
| 3,558,006 | A | * | 1/1971 | Redmond ................. | A47F 1/10 221/150 HC |
| 4,986,442 | A | * | 1/1991 | Hinterreiter ....... | B65D 83/0418 221/197 |
| 5,460,295 | A | * | 10/1995 | Law .................... | B65D 83/0418 221/185 |
| 6,564,967 | B1 | * | 5/2003 | Stringfield ......... | B65D 83/0418 221/229 |
| 7,922,971 | B2 | * | 4/2011 | Bryer ................. | A61B 5/14532 422/50 |
| 7,935,307 | B2 | * | 5/2011 | Angelides ........ | G01N 33/48757 422/401 |
| 8,523,011 | B2 | * | 9/2013 | Haas .................. | B65D 83/0418 206/540 |
| 8,905,964 | B2 | * | 12/2014 | Poutiatine ............. | A61J 7/0038 604/59 |

(Continued)

*Primary Examiner* — Gene O Crawford
*Assistant Examiner* — Kelvin L Randall, Jr.

(57) ABSTRACT

The present invention relates to a test-strip storage vial, comprising a vial body, a test-strip storing chamber, a button pole, and a baffle; wherein the test strip storing chamber is disposed inside the vial body; wherein the button pole is provided at the side of the vial body and capable of moving vertically; wherein the baffle is provided at one end of the storing chamber and capable of moving horizontally, wherein a top-lifted unit is provided at another end of the storing chamber; wherein the top-lifted is capable of vertically supporting test strips disposed in the storing chamber and enables the test strips to move towards the baffle; wherein the button pole is connected to the baffle through a flexible part; wherein the baffle is connected to the vial body through an elastic part; wherein the test strip is ejected by the horizontal movement of the baffle.

14 Claims, 3 Drawing Sheets

(56) References Cited

U.S. PATENT DOCUMENTS

| | | | | |
|---|---|---|---|---|
| 8,961,432 B2* | 2/2015 | Shaanan | ............ | A61B 5/15113 600/583 |
| 2004/0007585 A1* | 1/2004 | Griffith | ............ | G01N 33/48757 221/232 |
| 2005/0281706 A1* | 12/2005 | Funke | .............. | G01N 33/48757 422/63 |
| 2007/0095293 A1* | 5/2007 | Moulton | .............. | A01K 5/0114 119/51.01 |
| 2011/0127269 A1* | 6/2011 | Bucholtz | ............. | B65D 43/162 220/378 |
| 2014/0014677 A1* | 1/2014 | Chan | .................. | A61B 5/14532 221/232 |
| 2015/0136801 A1* | 5/2015 | Fisher, Jr. | .............. | B43M 99/00 221/268 |

\* cited by examiner

TEST-STRIP STORAGE VIAL

BACKGROUND

Field of Invention

The present invention relates to the field of storage devices, and more particularly, to a test-strip storage vial.

Description of Related Art

In biological and chemical fields, test strips are frequently used in the process of experimentation and testing. Additionally, test strips are also needed in medical testing procedures. The accessibility of test strips is crucial in all the process.

Most common test-strip storage vial is a plastic bottle with ordinary screw cap. When accessing the test strip, people have to unscrew the bottle cap then take out the test strip. The bottle cap must be fastened quickly after use to avoid exposure to moisture causing the failure of the test strips.

The repeated operation of opening and closing the bottle cap can also reduce the efficiency of the testing process. Meanwhile, the test strips in the bottle can be affected by the moisture in the surrounding environment and fail to function normally. When the storage device is used for testing the blood glucose, the first step is to prick a finger using a blood taking needle, then collect a blood sample using the test strip. Under such circumstance, the user can only access the test strip with only one hand. As a result, it's very inconvenient to open the bottle cap. Additionally, the test strip may be contaminated by the sweat or other impurities on user's hand thus producing inaccurate test results Accordingly, accessing the test strip by using hands is not ideal, and using a conventional screw-cap plastic bottle can be inconvenient.

In conclusion, the inconvenience of accessing and high risk of contamination of test strips are urgent problems need to be solved for those skilled in this field.

SUMMARY OF THE INVENTION

The present invention provides a test-strip storage vial, of which the structure design can effectively solve the issues relating to inconvenient accessing and contamination by moisture in the air and dirt on the hand.

In order to achieve the objectives above, the present invention provides the following technical solution.

A test-strip storage vial, comprising a vial body and a test-strip storing chamber provided in the vial body. A button pole which can move vertically is provided at the side of the vial body. A baffle which can move horizontally is provided at one end of the storing chamber on the vial body and a top-lifted unit is provided at another end of the storing chamber on the vial body. The top-lifted unit is used to vertically support the test strips and enable the test strips to move towards the direction of the baffle. The button pole is connected to the baffle through a flexible part and the baffle is connected to the vial body through an elastic part. The button pole moves vertically under the action of the external force so as to push out the test strips from the vial body horizontally through the horizontal movement of the baffle driven by the flexible part. The baffle can be recovered to the original position by the elastic part so as to recover the button pole to the original position through the flexible part when the button pole is not affected by the external force.

It is preferred that, in the above test-strip storage vial, the vial body comprises an upper cover and a fixedly-connected lower vial body which can be detachable from the upper cover. The elastic part is in detail a spring.

It is preferred that, in the above test-strip storage vial, the elastic part is in detail a wire rope. The test-strip storage vial comprises a fulcrum pin so that the wire rope can twine around and the two ends of the fulcrum pin are fixedly-connected to the lower vial body.

It is preferred that, in the above test-strip storage vial, a sliding chute is provided inside of the lower vial body and the button pole is glidingly connected to the sliding chute.

It is preferred that, in the above test-strip storage vial, the lower vial body comprises an inner cover and a sliding chute for the baffle is provided on the top surface of the inner cover. The baffle vertically moves throughout the top surface of the inner cover.

It is preferred that, in the above test-strip storage vial, the inner cover comprises a tightly-compressing protruded part which can push the surface of test strips tightly and the bottom surface of the baffle is lower than that of the tightly-compressing protruded part.

It is preferred that, in the above test-strip storage vial, the inner cover comprises a vertically-directional guiding chute and the top-lifted unit slides along the guiding chute.

It is preferred that, in the above test-strip storage vial, the top-lifted unit comprises a top-lifted block and two top-lifted springs. The top-lifted springs are connected between the top-lifted block and the vial body.

It is preferred that, in the above test-strip storage vial, the bottom surface of the top-lifted block is provided with supporting legs and the top-lifted springs are covered on the supporting legs; two connecting poles with recess holes are provided in the vial body so that the supporting legs can insert into the recess holes in the connecting poles.

It is preferred that, in the above test-strip storage vial, the top-lifted block comprises a recess hole for storing drying agent.

The present invention provides a test-strip storage vial, comprising a vial body and a test-strip storing chamber in the vial body. A button pole which can move vertically is provided at the side of the vial body. A baffle which can move horizontally is provided at one end of the storing chamber on the vial body and a top-lifted unit is provided at another end of the storing chamber on the vial body. The top-lifted unit is used to vertically support the test strips and enable the test strips to move towards the direction of the baffle. The button pole is connected to the baffle through a flexible part and the baffle is connected to the vial body through an elastic part. The button pole moves vertically under the action of the external force so as to push out the test strips from the vial body horizontally through the horizontal movement of the baffle driven by the flexible part. The baffle can be recovered to the original position by the elastic part so as to recover the button pole to the original position through the flexible part when the button pole is not affected by the external force. When using the test-strip storage vial, a right amount of test strips should be pre-stored and horizontally stacked up in the storing chamber. The top-lifted unit is in compressed state due to the storage of a certain number of test strips. In such a way, the lifting force can be provided to the top-lifted unit so that the baffle can easily contact with the side of the test strips. After that, the button pole can be pressed to drive the baffle to move towards the side of the test strips through the flexible part. When the baffle pushing the side of the test strips tightly, relaxes the button pole and the tensile force of the flexible part enables the baffle to push out the test strip. After pushing to a certain length, the test strip can be inserted into the corresponding testing equipment. After taking out the test strip completely, the top-lifted unit can be further lifted by the elastic force to lift the test strip required for next test to the position where can be pushed out by the baffle.

The test-strip storage vial of the present invention can be capable of driving the baffle to reciprocate horizontally through the vertical movement of the button pole connected to the flexible part of the baffle so as to push out the test strips from the test-strip storage vial. After that, the test strip can be inserted into corresponding testing equipment for preparation of next test, improving the efficiency of taking out a test strip from the test-strip storage vial significantly. The related persons no longer need to grab a test strip from the depth of the test-strip storage vial so that increases the automation degree of the test-strip storage vial. Meanwhile, the whole process can be completed by the baffle without touching with the hand, protecting the test strip from being contaminated by other impurities or sweat on the hand. Besides, the test-strip storage vial can allow batch supplement of test strips every time after finishing all without opening or closing the vial body frequently so as to prevent the test strips from being exposed to the moisture and prolong the effective status of the test strips accordingly. The test strip can be taken out just by pressing then relaxing the button pole, which brings great convenience for the single-handed operations of related persons.

BRIEF DESCRIPTION OF THE DRAWINGS

To clearly expound the present invention or the technical solution, the drawings and embodiments are hereinafter combined to illustrate the present invention. Obviously, the drawings are merely some embodiments of the present invention and those skilled in the art can associate themselves with other drawings without paying creative labor.

MARKING INSTRUCTION OF THE DRAWINGS

Upper Cover 1、 Inner Cover 2、 Lower Vial Body 3、 Button Pole 4、 flexible part 5、 Fulcrum Pin 6、 Baffle 7、 elastic part 8、 Test Strip 9、 Top-lifted Block 10、 Top-lifted Spring 11、 Supporting Leg 12、 Drying Agent 14、 Tightly-compressing Protruded Part 15.

DETAILED DESCRIPTION

The present invention provides a test-strip storage vial, which facilitates the accessing of the test strips and prevents the test strips from being contaminated by surroundings.

Drawings and detailed embodiments are combined hereinafter to elaborate the technical principles of the present invention. The description is intended to illustrate, but not to limit the protective scope of the present invention in any way. Based on the detailed description herein, those skilled in the art can associate themselves with other particular embodiments without paying creative labor. Thus, these embodiments shall all fall within the protective scope of the present invention.

Figure 1:
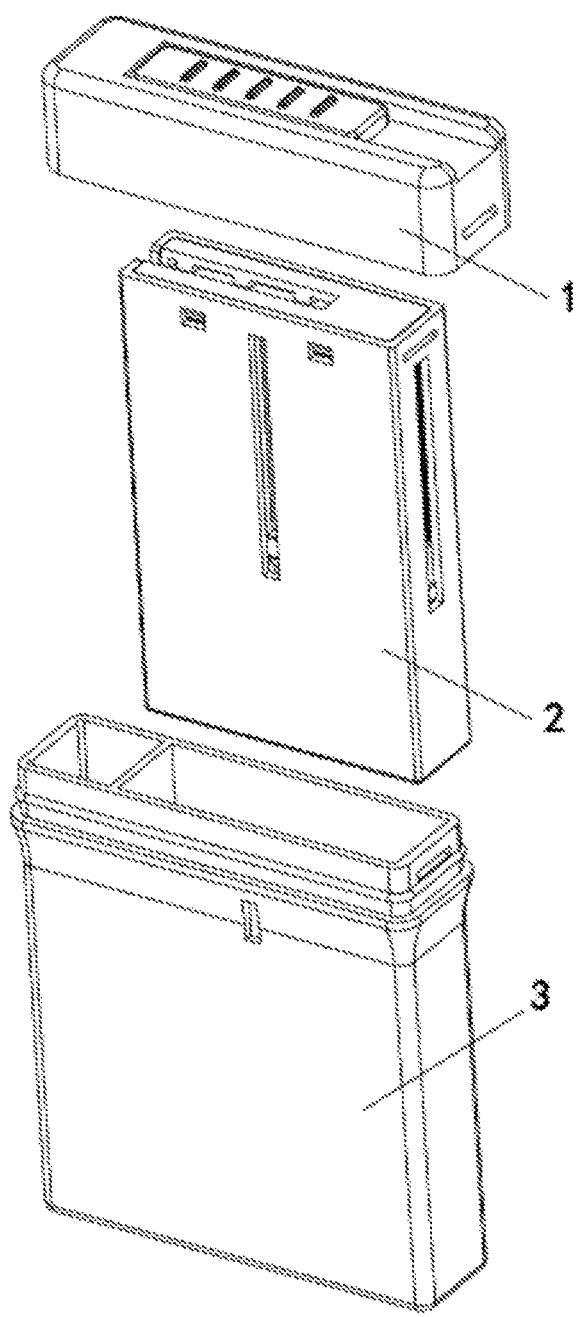
FIG. 1 is an outside view of the test-strip storage vial in the embodiment of the present invention.
Figure 2:
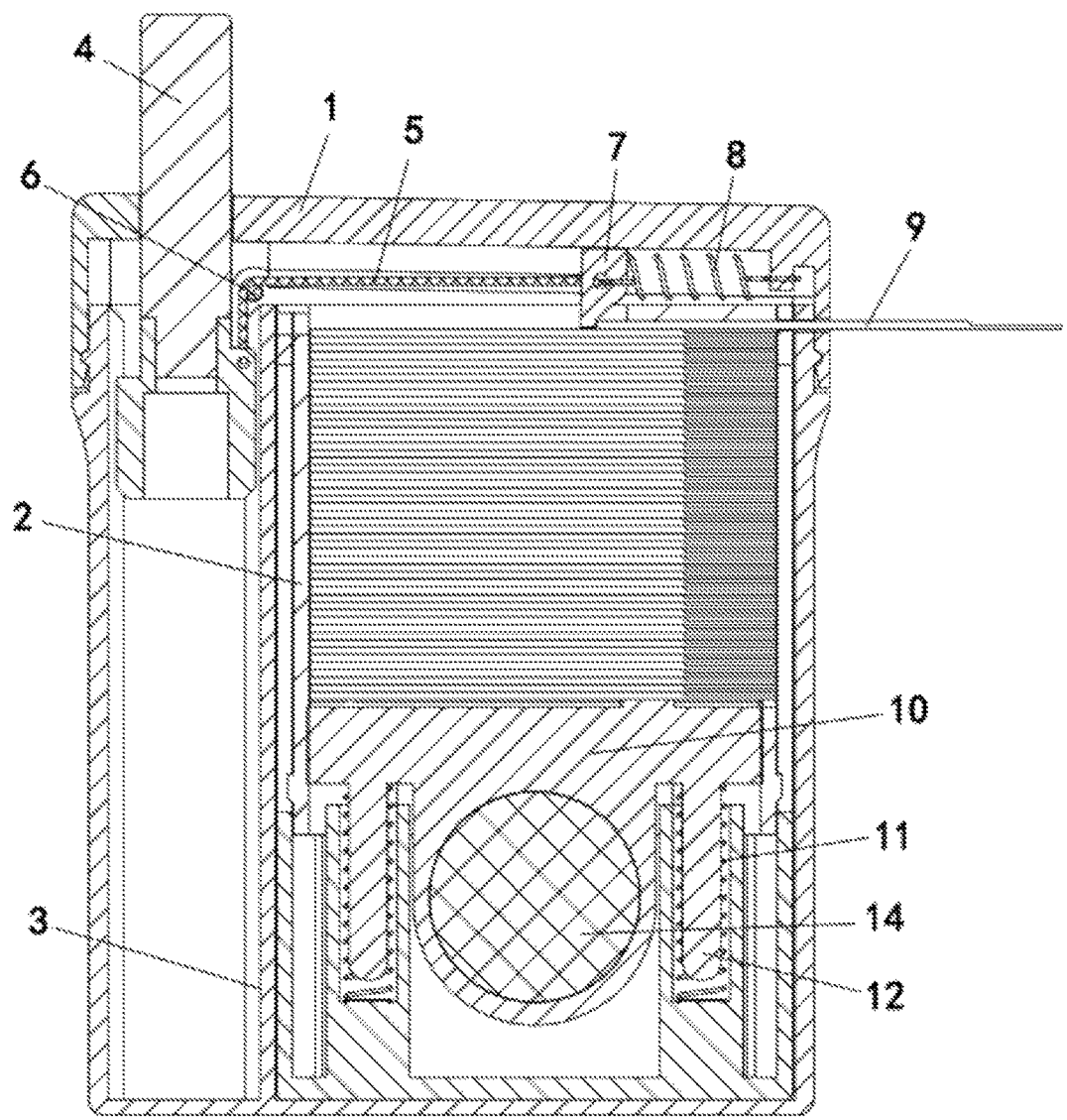
FIG. 2 is a front view structural schematic diagram of the test-strip storage vial in the embodiment of the present invention.

Referring to FIG. 1 and FIG. 2, FIG. 1 is an external view of the test-strip storage vial in the embodiment of the present invention and FIG. 2 is a structural schematic diagram of the test-strip storage vial in the embodiment of the present invention.

In one embodiment, the test-strip storage vial comprises a vial body and a test-strip 9 storing chamber inside of the vial body; the internal shape of the storing chamber is preferred to match the shape of the stacked test-strips 9 to prevent the test strips 9 from moving inside of the vial body. A button pole 4 capable of moving vertically is provided at one side in the vial body, wherein the top surface of the button pole 4 is preferred to be formed into the shapes which allows user's finger to press multiple times without discomfort. In one embodiment, the top surface of the button pole can be a round shape. A baffle 7 which capable of moving horizontally is provided at one end of the storing chamber on the vial body, and a top-lifted unit is provided at another end of the storing chamber in the vial body. The top-lifted unit further comprises an elastic supporting part, which is used to vertically support the test strips 9 and enable the test strips 9 to move in a direction towards the baffle 7. The button pole 4 is connected to the baffle 7 through a flexible part 5 and the baffle 7 is connected to the vial body through an elastic part 8. The button pole 4 moves vertically under the action of the external force so as to push out the test strips 9 from the vial body horizontally through the horizontal movement of the baffle 7 driven by the flexible part. In this embodiment, the downward movement of button pole 4 bringing the baffle 7 to the side of the storing chamber next to the button pole 4. As external force is released, elastic part 8 pulls the baffle toward its original position on the side of the storing chamber opposite of the button pole 4. As the baffle 7 recovers to its original position, it pushes one test strip 9 out of the storing chamber.

In this embodiment, the test-strip storage vial of the present invention is capable of driving the baffle 7 horizontally through the vertical movement of the button pole 4 connected to the flexible part of the baffle 7 to push out the test strips 9 from the test-strip storage vial. After that, the test strip 9 can be inserted into the corresponding testing equipment for testing. The user no longer needs to grab a test strip 9 from the depth of the test-strip storage vial due to the automation of the test-strip storage vial. Meanwhile, the process of ejecting the test strip 9 is completed by the movement of baffle 7 alone, protecting the test strip 9 from being contaminated by impurities on the hand. Additionally, the test-strip storage vial allows batch refill of test strips 9 once the storing chamber is empty without the need to open or close the vial body frequently preventing the test strips 9 from being exposed to the moisture and prolonging the effectiveness of the test strips 9. Furthermore, since the test strip 9 can be taken out just by pressing then relaxing the button pole 4, it enables single-handed operations of user resulting in convenience of operation.

In one embodiment, the vial body comprises an upper cover 1 and a fixedly-connected lower vial body 3 which can be detachable from the upper cover 1. In one embodiment, the type of connection is a threaded connection with a self-lock structure or other connection types such as buckle connection. The elastic part 8 is can be a spring. The vial body is preferred to comprise an upper cover 1 and a lower vial body 3 so the users can open or close the vial body conveniently and making refill of the test strips 9 efficient. After filling the test strips, the upper cover 1 is closed to protect the test strips 9 from being affecting by the moisture in the air and to prolong the life-span of the test strips 9.

In one embodiment, the flexible part 8 is a wire rope. The test-strip storage vial comprises a fulcrum pin 6 wherein the flexible part 5 can twine around the fulcrum pin 6 fixedly-connected to the lower vial body 3. The flexible part 5 twines from the top of the fulcrum pin 6 so that one segment of the wire rope 5 fixedly-connected to the button pole 4 is in vertical position and another segment of the wire rope 5 fixedly-connected to the baffle 7 is in horizontal position. The fulcrum pin 6 allows the vertical and horizontal movement of the wire rope 5 to be more precise, also reduces friction between the wire rope 5 and the test-strip storage vial. Additionally, the rotation of the fulcrum pin 6 facilitates the movement of the flexible part 5, prolongs the life-span of the flexible part 5, and allows the movement of the baffle 7 to be more smoothly.

In one embodiment, the interior of the vial body 3 comprises a sliding chute and the button pole 4 is glidingly connected to the sliding chute. It is preferred that the sliding chute is constructed in a way that allows the button pole 4 to be pressed down and to rebound smoothly to ensure the button pole 4 in the vertical direction.

Figure 3:
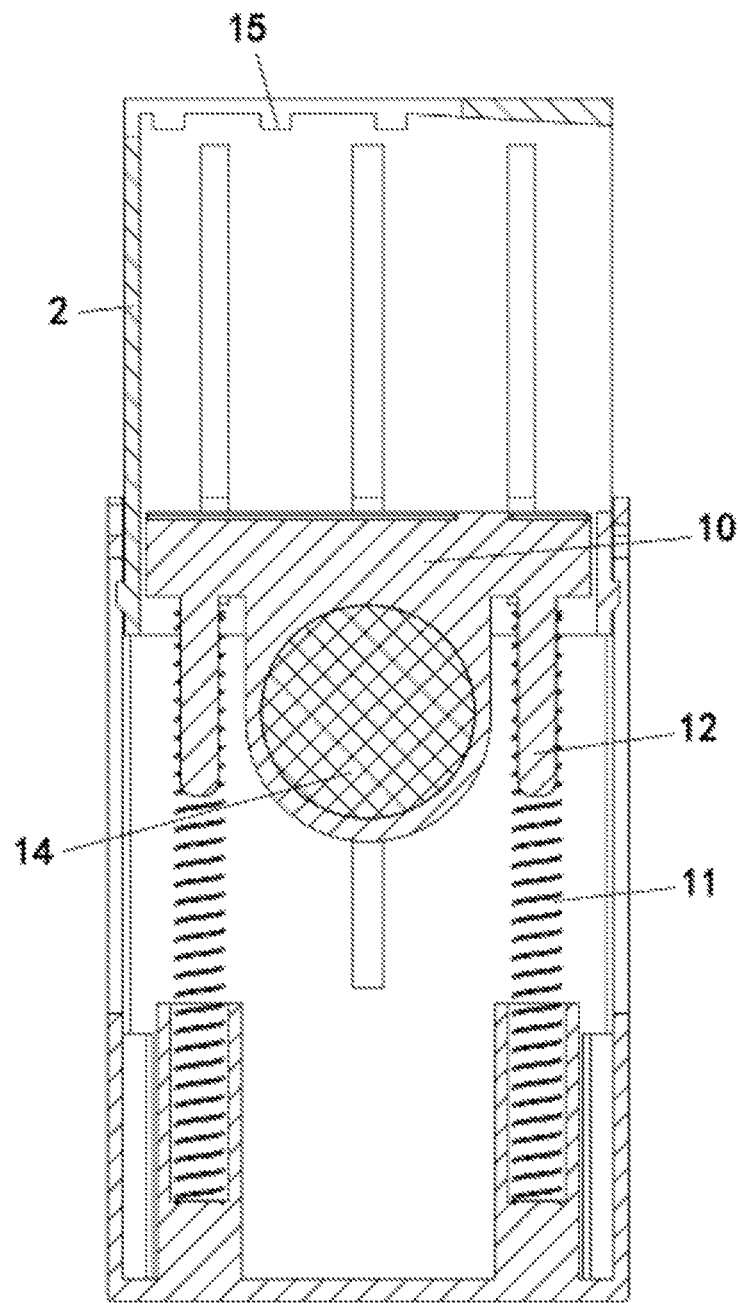
FIG. 3 is a front view structural schematic diagram of the lower vial body in the embodiment of the present invention.

Referring FIG. 3, the lower vial body 3 comprises an inner cover 2, the inner cover 2 further comprising a sliding chute for the push plate 6; the sliding chute allows the push plate 6 to slide horizontally along with the push button 4 and push the test strip 9 out of the storing chamber, wherein the push plate 6 slides protrude through the sliding chute and extends vertically into the storing chamber; the upper cover 1 comprises a down-pressing unit, which pushes the inner cover 2 tightly. In one embodiment, the inner cover 2 can be removed integrally and the space for storing the test strips 9 can be exposed so that the refilling of the test strips 9 becomes more convenient.

In one embodiment, the inner cover 2 comprises a tightly-compressing protruded part 8 and the bottom surface of the push plate 6 is lower than that of the tightly-compressing protruded part 8. The tightly-compressing protruded part 8 is preferred to be located on the inner top surface of the inner cover 2, wherein there can a plurality of protruded parts 8. The bottom surface of the push plate 6 is lower than that of the tightly-compressing protruded part 8, ensuring the push plate 6 to be in contact with the test strip 9. In this embodiment, the tightly-compressing protruded part 8 maintains the test strips at a certain height. There can be a plurality of tightly-compressing protruded part 8 to keep the test strips 9 uniformly at a horizontal position. The tightly-compressing protruded part 8 can be made in a variety of shapes.

In one embodiment, the inner cover 2 comprises a vertically-directional guiding chute. The guiding chute is preferred to be located on the side faces of the inner cover 2. The top-lifted unit slides along the guiding chute. The guiding chute enables the top-lifted unit to be raised and lowered stably inside the inner cover 2 and effectively prevents the test strip 9 from jammed in the passage due to the inclination of the top-lifted unit. The guiding chute also limits the position of the top-lifted unit, inhibiting the top-lifted unit from falling to the bottom or bouncing out of the inner cover 2 to make the assembly and disassembly process and the access to test strip 9 more convenient In one embodiment, the top-lifted unit further comprises a top-lifted block 10 and two top-lifted springs 11. The top-lifted springs are disposed between the top-lifted block 10 and the vial body. The test strips 9 are disposed on top of the top-lifted block 10, and the top-lifted springs 11 provides tensile force to push the top-lifted block in the direction away from the bottom of the vial body.

In one embodiment, the top-lifted unit comprises a plurality of supporting legs 12, wherein the number of the plurality of the supporting legs 12 are preferred to be an even number arranged symmetrically according to the shape of the top-lifted unit 10. The supporting legs 12 are disposed inside top-lifted springs 11. The vial body comprises connecting poles with recess holes, wherein the supporting legs 12 and the top-lifted springs 11 are disposed in the recess holes of connecting poles. The supporting legs 12 enables the top-lifted springs 11 to be connected to the top-lifted block 10 in a stable manner and the symmetrically arranged even-numbered supporting legs 12 ensure that the top-lifted block 10 are in a horizontal position without inclination or distortion.

In one embodiment, the top-lifted block 10 further comprises a recess hole for storing the drying agent 14. In this embodiment, drying agent 14 is placed in the recess hole to absorb moisture in the small amount of air in the storage and keeps the test strip 9 in dry state prevent malfunction of the test strips 9 due to dampness.

Each embodiment of the description is illustrated by adopting progressive way and the emphasis of each embodiment is different from the others. The similarity of each embodiment can be cross-referenced.

The description of above embodiments allows those skilled in the art to realize or use the present invention. Without departing from the spirit and essence of the present invention, those skilled in the art can combine, change or modify correspondingly according to the present invention. Therefore, the protective range of the present invention should not be limited to the embodiments above but conform to the widest protective range which is consistent with the principles and innovative characteristics of the present invention.

The invention claimed is:
1. A test-strip storage vial, comprising:
a vial body,
a test-strip storing chamber,
a button pole, and
a baffle;
wherein the test strip storing chamber is disposed inside the vial body; wherein the button pole is provided at the side of the vial body and capable of moving vertically; wherein the baffle is provided at one end of the storing chamber and capable of moving horizontally, wherein a top-lifted unit is provided at another end of the storing chamber; wherein the top-lifted unit is capable of vertically supporting test strips disposed in the storing chamber and enables the test strips to move towards the baffle; wherein the button pole is connected to the baffle through a flexible part; wherein the baffle is connected to the vial body through an elastic part; wherein the button pole is capable of moving vertically under external force driving the baffle to move horizontally; wherein the test strip is ejected by the horizontal movement of the baffle; wherein the vial body further comprising an upper cover and a fixedly-connected lower vial body, wherein the lower vial body can be detachable from the upper cover; wherein the elastic part is a spring; wherein the flexible part is a wire rope; wherein the test-strip storage vial further comprises a fulcrum pin fixedly connected to the lower vial body; wherein the wire rope twines around the fulcrum pin.
2. The test-strip storage vial of claim 1, wherein a sliding chute is provided inside of the lower vial body; wherein the button pole is glidingly connected to the sliding chute.
3. The test-strip storage vial of any claim in 1, wherein the lower vial body further comprising an inner cover; wherein a sliding chute is provided on the inner cover; wherein the baffle moves horizontally in said sliding chute.

4. The test-strip storage vial of claim 3, wherein the bottom surface of the baffle is lower than the lowest point of the tightly-compressing protruded part.

5. The test-strip storage vial of claim 4, wherein the inner cover further comprising a guiding chute; wherein the top-lifted unit slides along the guiding chute.

6. The test-strip storage vial of claim 1, wherein the top-lifted unit further comprising a top-lifted block and at least one top-lifted spring; wherein the top-lifted springs are disposed between the top-lifted block and the vial body.

7. The test-strip storage vial of claim 6, wherein the bottom surface of the top-lifted block further comprising at least one supporting leg and at least one connecting pole with a recess hole; wherein each supporting leg is disposed inside a top-lifted spring; wherein each supporting leg is inserted into a recess hole in the connecting pole.

8. The test-strip storage vial of claim 6, wherein the top-lifted block further comprising a recess hole for storing drying agent.

9. The test-strip storage vial of any claim in 1, wherein the lower vial body further comprising an inner cover; wherein a sliding chute is provided on the inner cover; wherein the baffle moves horizontally in said sliding chute.

10. The test-strip storage vial of any claim in 2, wherein the lower vial body further comprising an inner cover; wherein a sliding chute is provided on the inner cover; wherein the baffle moves horizontally in said sliding chute.

11. The test-strip storage vial of claim 9, wherein the bottom surface of the baffle is lower than the lowest point of the tightly-compressing protruded part.

12. The test-strip storage vial of claim 11, wherein the inner cover further comprising a guiding chute; wherein the top-lifted unit slides along the guiding chute.

13. The test-strip storage vial of claim 10, wherein the inner cover further comprising a tightly-compressing protruded part capable of keeping the surface of test strips in a horizontal position; wherein the bottom surface of the baffle is lower than the lowest point of the tightly-compressing protruded part.

14. The test-strip storage vial of claim 13, wherein the inner cover further comprising a guiding chute; wherein the top-lifted unit slides along the guiding chute.

* * * * *